(12) United States Patent
Ritoniemi

(10) Patent No.: US 11,930,569 B2
(45) Date of Patent: Mar. 12, 2024

(54) LED MATRIX LIGHTING DEVICE

(71) Applicant: Procemex Oy, Jyväskylä (FI)

(72) Inventor: Jari Ritoniemi, Lempäälä (FI)

(73) Assignee: Procemex Oy, Jyväskylä (FI)

(*) Notice: Subject to any disclaimer, the term of this patent is extended or adjusted under 35 U.S.C. 154(b) by 177 days.

(21) Appl. No.: 17/776,013

(22) PCT Filed: Nov. 16, 2020

(86) PCT No.: PCT/FI2020/050760
§ 371 (c)(1),
(2) Date: May 11, 2022

(87) PCT Pub. No.: WO2021/099680
PCT Pub. Date: May 27, 2021

(65) Prior Publication Data
US 2022/0400542 A1    Dec. 15, 2022

(30) Foreign Application Priority Data

Nov. 20, 2019   (FI) ...................................... 20195991

(51) Int. Cl.
*H05B 45/14*   (2020.01)
*F21K 9/69*    (2016.01)
(Continued)

(52) U.S. Cl.
CPC ............... *H05B 45/14* (2020.01); *F21K 9/69* (2016.08); *G01N 21/8986* (2013.01); *F21Y 2115/10* (2016.08)

(58) Field of Classification Search
CPC ........... H05B 45/14; H05B 45/12; F21K 9/69; G01N 2021/8816; G01N 2021/8902;
(Continued)

(56) References Cited

U.S. PATENT DOCUMENTS 5,172,005 A * 12/1992 Cochran ................. H04N 7/181
                                                          348/E7.086
5,936,353 A *  8/1999 Triner ...................... F21V 5/04
                                                          257/E25.02
(Continued)

FOREIGN PATENT DOCUMENTS

DE    102012006636 A1    5/2013
WO      2010003126 A2    1/2010
(Continued)

OTHER PUBLICATIONS

European Patent Office, Supplementary European Search Report, Application No. PCT/FI2020050760, dated Nov. 8, 2023, 12 pages.
(Continued)

*Primary Examiner* — Ryan Jager
(74) *Attorney, Agent, or Firm* — Ziegler IP Law Group

(57) ABSTRACT

An LED matrix lighting device for illuminating a lighting pattern with even intensity. The LED matrix lighting device includes a plurality of LEDs, a collimating lens in front of each LED for collimating light of the LED, and a light refracting element in front of collimating lenses arranged to refract light of at least a first part of the LEDs with a different refraction angle than at least a second part of the LEDs. The disclosure further relates to a machine vision system, a method, and a computer program product.

10 Claims, 5 Drawing Sheets

(51) Int. Cl.
  *G01N 21/898* (2006.01)
  *F21Y 115/10* (2016.01)
(58) Field of Classification Search
  CPC ............... G01N 21/8806; G01N 33/34; G01N 2021/8908; G01N 2201/062; G01N 2201/0638; G01N 21/8901; G01N 2021/8917; G01N 2201/0633; G01N 21/8914
  USPC .......................................................... 315/291
  See application file for complete search history.

(56) References Cited

U.S. PATENT DOCUMENTS

| | | | | |
|---|---|---|---|---|
| 6,207,946 | B1* | 3/2001 | Jusoh | G01N 21/8806 250/559.34 |
| 10,955,347 | B2* | 3/2021 | Ritoniemi | G01N 21/892 |
| 2006/0232436 | A1* | 10/2006 | Ding | G06K 7/10732 340/815.45 |
| 2015/0323152 | A1* | 11/2015 | Mayer | G03B 15/02 362/330 |
| 2018/0175262 | A1* | 6/2018 | Jansen | H01L 25/167 |
| 2019/0049381 | A1* | 2/2019 | Ritoniemi | D21G 9/0009 |
| 2022/0400542 | A1* | 12/2022 | Ritoniemi | F21K 9/69 |

FOREIGN PATENT DOCUMENTS

| | | |
|---|---|---|
| WO | 2012049370 A1 | 4/2012 |
| WO | 2014011665 A1 | 1/2014 |
| WO | 2017036900 A1 | 3/2017 |

OTHER PUBLICATIONS

Finnish Patent and Registration Office, Office Action, Application No. 20195991, dated Mar. 14, 2022, 7 pages.
Finnish Patent and Registration Office, Office Action, Application No. 20195991, dated Jun. 18, 2020, 7 pages.
International Search Report, Finnish Patent and Registration Office, Application No. PCT/FI2020/050760, dated Feb. 11, 2021, 6 pages.
Written Opinion of the International Searching Authority, Finnish Patent and Registration Office, Application No. PCT/FI2020/050760, dated Feb. 11, 2021, 9 pages.

* cited by examiner

LED MATRIX LIGHTING DEVICE

TECHNICAL FIELD

The aspects of the disclosed embodiments relate to an LED matrix lighting device arranged to create a uniform and even illumination pattern on a surface of a monitoring target, for example, a continuous wood fibre web. The aspects of the disclosed embodiments further relate to a machine vision system comprising at least one LED matrix lighting device, a method of utilizing the LED matrix lighting device and a computer program product causing a system to carry out the method.

BACKGROUND

In continuous manufacturing processes, for example, paper, pulp and cardboard machines, there are materials or products constantly formed and moving through the machine. In such processes, a plurality of cameras, for example, 10 to 40 cameras are used for monitoring the process in order to detect possible deviations or web breaks in different parts of machines. For imaging the continuous material web has to be illuminated. The paper web may move over 120 km/h and thus cameras have to use very short shutter speed times in order to stop motion. Therefore, the quality of the images from the moving web depends significantly on the illumination.

Nowadays, also LED lighting devices are often used for illuminating a moving web. The idea is to provide a uniform illumination pattern on the surface of the web. However, it is not always possible, because there is a lack of space above (or under) the moving web and thus it is not possible to mount an LED lighting device perpendicular to the paper web to be illuminated and monitored, but the web is illuminated from the side of the paper machine, often at an angle of 30 to 60 degrees to the paper web. Therefore, the illumination pattern may not be uniform, but different parts of the pattern have different brightness.

SUMMARY

Now there has been invented an improved method and technical equipment implementing the method. Various aspects of the disclosed embodiments include an LED matrix lighting device arranged to create a uniform and even illumination pattern on a surface of a monitoring target, for example, a continuous wood fibre web. The aspects of the disclosed embodiments further relate to a machine vision system comprising at least one LED matrix lighting device, a method of utilizing and controlling the LED matrix lighting device, and a computer program product causing a system to carry out the method and controlling the LED matrix lighting device.

According to a first aspect of the disclosed embodiments, there is provided an LED matrix lighting device for illuminating a lighting pattern with even intensity. The LED matrix lighting device comprises a plurality of LEDs, a collimating lens in front of each LED for collimating light of the LED, and a light refracting element in front of collimating lenses arranged to refract light of at least a first part of the LEDs with a different refraction angle than at least a second part of the LEDs.

According to an embodiment, the LED matrix lighting device further comprises at least one powering circuit of LEDs and an amount of current provided for the first part of LEDs is different than an amount of current provided for at least the second part of LEDs. According to an embodiment, the first part of LEDs comprises one LED, one line of LEDs of the LED matrix or one column of LEDs of the LED matrix. According to an embodiment, the refraction angle is determined based on the place of an LED in the LED matrix lighting device. According to an embodiment, a refraction angle is an angle between an optical central axis of collimated light of an LED and an optical central axis of the refracted light of the same LED. According to an embodiment, a FWHM viewing angle of the collimated light of LEDs is at least as large as the difference between the refraction angles. According to an embodiment, current provided for at least one LED is adjustable. According to an embodiment, current provided for at least one LED is adjustable based on detected intensity deviations in a captured image.

According to a second aspect of the disclosed embodiments, there is provided a machine vision system for detecting deviations from a wood fibre web, wherein the machine vision system comprises: an LED matrix lighting device according to the first aspect and its embodiments, at least one imaging device for capturing images of the illuminated area, and a data processing device.

According to an embodiment, the data processing device is arranged to analyse image data for detecting intensity deviations in the captured images. According to an embodiment, the data processing device is arranged to adjust current provided for at least one LED based on detected intensity deviations.

According to a third aspect of the disclosed embodiments, there is provided method comprising: obtaining image data, analyzing image data, detecting intensity deviations in an illumination pattern provided by an LED matrix lighting device according to the first aspect and its embodiments in the captured images, and adjusting current provided for at least one LED of the LED matrix lighting device.

According to a fourth aspect of the disclosed embodiments, there is provided a computer program product embodied on a non-transitory computer readable medium, comprising computer program code configured to, when executed on at least one processor, cause a system to perform the method comprising: obtaining image data, analyzing image data, detecting intensity deviations in an illumination pattern provided by an LED matrix lighting device according to the first aspect and its embodiments in the captured images, and adjusting current provided for at least one LED of the LED matrix lighting device.

BRIEF DESCRIPTION OF THE DRAWINGS

In the following, various embodiments of the present disclosure will be described in more detail with reference to the appended drawings, in which FIG. 1a, b show optical axes of LEDs of a prior art LED matrix lighting device from above and from the side;

FIG. 3b shows an exploded view of the LED matrix lighting device of FIG. 3a;

DETAILED DESCRIPTION

Figure 1A:
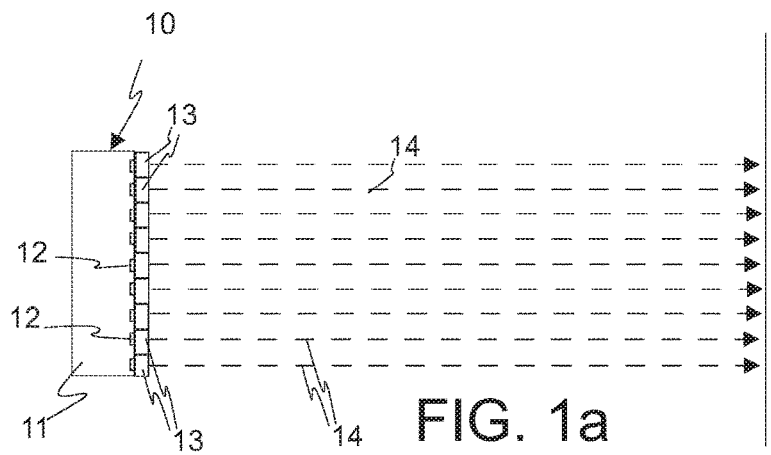
FIG. 1c, d show viewing angles of LEDs of the LED matrix lighting device of FIGS. 1a and 1b, correspondingly.

In continuous manufacturing processes, for example, paper, cellulose and cardboard machines, there are materials or products constantly formed and moving through the machine. A machine vision system comprising a plurality of cameras, for example 10 to 40 cameras, may be used for monitoring a process in different parts of the process. Monitoring may comprise imaging of a monitoring target, for example, a moving web, storing the image data and analyzing the image data. A camera, i.e. an image sensor, may be, for example, a CMOS or CCD camera, a matrix or line scan camera, a black and white or colour camera, a regular or smart camera, or any suitable camera.

For imaging the monitoring target, the monitoring target has to be illuminated. For example, for imaging a web product, the web product has to be illuminated, for example, by an illumination pattern or line having a width corresponding to the width of the web product. The term "web product", i.e. "web", refers in this context to any type of a wood fibre web produced by paper, cellulose or cardboard machines and the term "wood fibre" refers in this context to any suitable wood fibre, for example, paper, cellulose or cardboard fibre. The wavelength of the light used can vary over a wide spectrum depending on the monitoring target and/or the monitoring system, the wavelength may vary from the ultraviolet (UV) region up to the short wave infrared thermal region (SWIR).

As already stated above, suitable lighting may depend on monitoring targets, but a uniform illumination pattern with an even intensity throughout the pattern illuminated on a monitoring target provides a good starting point for high quality imaging, because it improves the probability of detecting a predetermined object of interest, for example deviation(s) or web break(s) in a web product. The type of lighting devices, the number of lighting devices, the direction of lights, the operation of lighting devices or lighting devices being used may depend on the object arranged to be imaged and the type of camera(s) used. A lighting device used for illuminating a monitoring target, for example a web, usually comprises at least two, several or a plurality of light sources, for example LEDs. LEDs need at least one LED circuit, LED driver or current source circuits, which are electronic circuits arranged to power LEDs i.e. powering circuits. Usually one electronic circuit powers several or a plurality of LEDs. The powering circuit is arranged to provide such a current through an LED(s) that the LED reaches a required or desired intensity for the light, and to limit the current to prevent damaging the LEDs. Although LEDs are discussed throughout the application, other suitable light sources may be used instead of LEDs.

Image data of captured images may be stored and analysed by a data processing device of each camera, for example a smart camera, used for imaging the manufacturing processes and/or image data of captured images may be transmitted to an external data processing device for storing and analysing. The external data processing device is a data processing device that is not an integrated part of a camera. The data processing devices monitor the data in order to find predetermined objects of interest. It is also possible to store and analyse image data in a system comprising both above mentioned systems i.e. a camera(s) with an integrated data processing device(s) and an external data processing device(s). All systems, cameras with integrated data processing devices, cameras with external data processing devices and combinations thereof, comprise or are connected to a database, user interface and possible interfaces to factory systems and manufacturing processes.

Cameras that capture images of continuous manufacturing processes may be a part of a Web Monitoring System (WMS) monitoring web breaks. The Web Monitoring System may continuously store the image data received from the plurality of cameras in a memory of a computer program product. This stored image data may be used for determining the causes of a paper web break after a web break has occurred. As the paper web may move over 120 km/h, cameras have to use very short shutter speed times in order to stop motion. Therefore, the quality of the images captured from the web moving that fast depends significantly on the even intensity of lighting and how the lighting is distributed in the image area.

Cameras may also be a part of a Web Inspection System (WIS) that is an event capturing camera system monitoring possible web deviations. The term "web deviation" in this context includes any deviation detectable from the web product, for example, a defect, a hole, a stain, a definite change, a grey or dark spot, a streak, a wrinkle, an air bubble or a pattern in a web product. In a Web Inspection System cameras are mounted to capture the entire web width in the cross direction of the paper web and to store the captured image data. Used illumination may be, for example reflection light or the web may be illuminated through the web. The angle of reflection light may also vary widely, depending on the defects of the paper web it is supposed to be looking for. But again, the quality of images depends on the quality of lighting.

Based on the above, it is clear that lighting is an important part of quality process monitoring. Therefore, the idea of the present disclosure is to provide a lighting device that provides such conditions that detecting a predetermined object from captured images is as efficient as possible.

A lighting device according to example embodiments of the present disclosure is a matrix type light emitting LED lighting device i.e. an LED matrix lighting device that is configured to create a uniform illumination pattern with an even luminous intensity i.e. brightness throughout the pattern on the surface of a monitoring target, for example, on a web product. The LED matrix lighting device may comprise a base, LEDs, at least one powering circuit for LEDs, collimating lenses, and a light refracting element. LEDs are arranged in the form of a matrix on the surface of the base, for example by attaching a circuit board(s) or other surface or substrate, into which LEDs are attached on the surface of the base.

A powering circuit is arranged to provide current through the LEDs so that they illuminate at the required or desired intensity. A part of the LEDs may be driven differently than at least one other part of the LEDs i.e. the powering circuit may provide a different amount of current to one part of the LEDs than at least one other part of the LEDs. It is also possible that each LED is driven differently than other LEDs, or a column of LEDs of an LED matrix is driven differently than at least one other column of LEDs of the LED matrix, or a line of LEDs of an LED matrix is driven differently than at least one other line of LEDs of the LED matrix. The provided amount of current may depend on, for example, the position of the LED in the matrix i.e. where the light beam of the LED is arranged to be directed to i.e. refracted by a light refracting element i.e. which part of the surface the light of the LED is arranged to illuminate taking into account the parts of the surface illuminated by the light positions of the other LEDs. For example, if the distance of a first part of the LEDs (e.g. a column of LEDs) is longer relative to the illuminating surface than at least one other part of the LEDs (other column(s)), the LEDs of the first part are refracted so that a greater refraction angle forms between an optical central axis of the LED light beam (before the light beam is refracted due to the refracting element) and the optical central axis of the refracted LED light beam, and the provided amount of current for the first part of the LEDs may be higher than the current provided for at least one other part of the LEDs, because the higher current makes these LEDs brighter, and, despite the longer distance to the surface, the first part of the LEDs may now illuminate the surface similarly to the at least one other part of the LEDs that are closer to the surface and driven by lower current. The amount of provided current may be controlled by a data processing device integrated in the LED matrix lighting device or by an external data processing device, for example, a data processing device that also analyses the image data of captured images or a user may control the amounts of provided current by configuring current amounts for LEDs.

A collimator is an optical element that collects the light rays from the LED and refracts them to become parallel rays. A collimator may be constructed by a parabolic mirror or lens and the LED may be positioned at its focal point. A collimating lens may be arranged in front of each LED i.e. there is a matrix of collimators, collimating lenses, attached on the LED matrix to collimate the output light from LEDs of the LED matrix. However, it is possible that a collimating lens is an integrated structure of an LED, in which case a separate collimating lens is not needed on the LED. An LED and a collimating lens together define the viewing angle of the LED i.e. the LED light beam angle indicating the usable light emitted from an LED source. The viewing angle may be defined by using Full Width at Half Maximum (FWHM) method, and it may be indicated by degrees. The FWHM defines the angle at which 50% of the peak intensity is reached. For example, if an LED was measured to have 50% intensity at the angle of 40°, the viewing angle of the LED (FWHM) would be 40°.

The light refracting element is arranged in front of each collimating lens in a form of a matrix of refracting lenses attached on the LED matrix so that each LED has a collimating lens and a refracting lens or as a single refracting lens attached on all LEDs of the LED matrix. The lens of the refracting lens matrix may be, for example a prism, for example, a Fresnel prism, and the single refracting lens may be, for example, a membrane or film forming a Fresnel-type lens or prism. The light refracting element is arranged to direct i.e. refract a central optical axis of each collimated LED light beam incrementally outwards from the optical central axis of the collimated LED light. The refracting element is configured to direct the light beams of LEDs to a wider area so that they do not direct the light to the same area on the surface of a monitoring target or so that illuminated areas on the surface overlap very little. Non-overlapping light beams i.e. refracted light beams enable forming of a uniform illumination pattern with an even luminous intensity i.e. brightness throughout the pattern on the surface of a monitoring target, because the current provided to LEDs is controlled and because current controlling has an effect on the intensities of illuminated areas. If light beams overlap, current controlling of LEDs has no effect on the illumination pattern or it is at least not as efficient as it is when each LED illuminates its own area in the illumination pattern, because same area is illuminated by several LEDs.

Figure 1B:
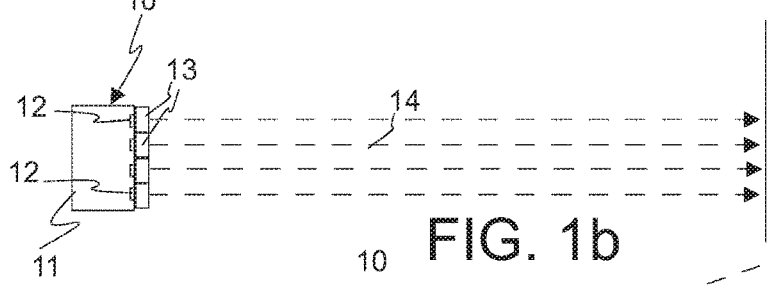

FIG. 1a shows optical axes 14 of LEDs 12 of a prior art LED matrix lighting device 10 from above i.e. horizontal optical axes of the LED matrix lighting device 10 is shown. The LED matrix lighting device 10 comprises a base 11, an LED matrix, and a collimator matrix. The LED matrix has a size of 9*4 i.e. there are 36 LEDs 12 in the LED matrix of the LED matrix lighting device 10. Electronic circuits of the LEDs 12 of the matrix lighting device are arranged in the base 11. The collimator matrix is arranged on the LEDs 12 and has also a size of 9*4. Each collimator lens 13 of collimator matrix is an optical element that collects the rays from the LEDs 12 and refracts them to become parallel rays shown as optical axes 14. FIG. 1b shows optical axes 14 of LEDs 12 of the prior art LED matrix 10 from the side i.e. vertical optical axes of the LEDs 12 is shown. As can be seen from FIGS. 1a and 1b, each optical axis 14 continues straight from the LEDs 12 i.e. they are not refracted.

Figure 1C:
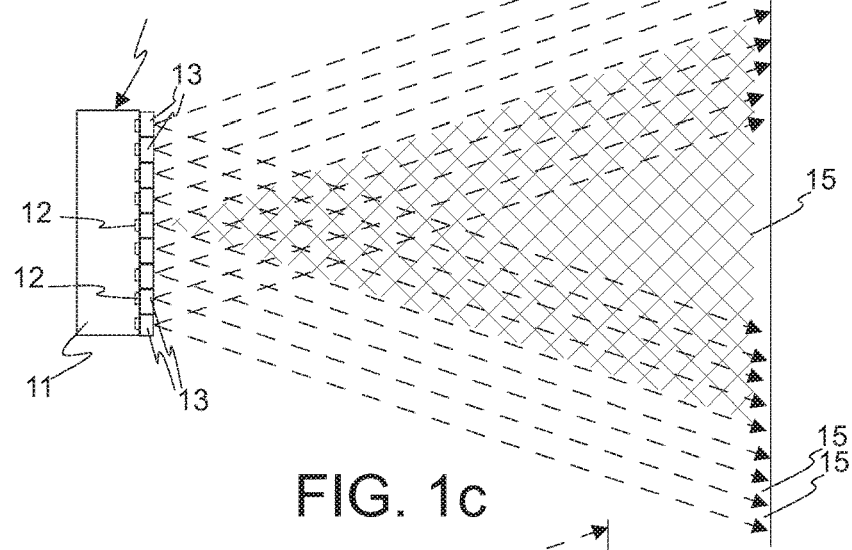
Figure 1D:
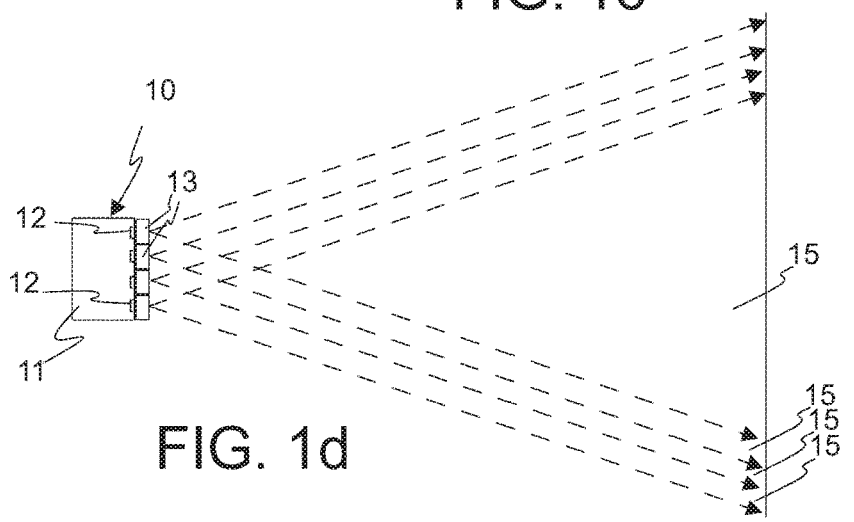

FIG. 1c shows viewing angles of LEDs 12 of the LED matrix lighting device 10 of FIG. 1a from above and FIG. 1d shows viewing angles of LEDs 12 of the LED matrix lighting device 10 of FIG. 1b from a side. Viewing angle 15 of an LED 12 has a conical shape; at first, it has a narrow shape that widens as the light extends away from the LED 12. The Full Width at Half Maximum (FWHM) viewing angles of LEDs 12 are 40 degrees. In order to achieve uniform illumination pattern over the whole web from the side of the web, FWHM (Full Width at Half Maximum) viewing angle of each LED of the lighting device must be wide, for example, 20-60 degrees.

The viewing angle 15 of the middle LED 12 is indicated by line pattern. Because optical axes 14 of LEDs is straight and extend parallel, the viewing angles of LEDs 12 overlap when a certain distance from the LEDs is achieved and thus the formed illumination pattern on the surface 16 has an uneven luminous intensity; the central area of the illumination pattern is illuminated by several LEDs 12, all LEDs in this embodiment, and the outermost part of the pattern is illuminated only by light produced by one LED. Therefore the central area of the illuminated line or pattern is brighter than the edge areas and different parts of the paper web are illuminated with different intensity, depending on, for example, the distance of the part from the central part of an illumination pattern; near the central of the illumination pattern there is bright light, but the amount of light is lower on the edge area of the illumination pattern. In addition, even if the LED currents of this prior art lighting device 10 were adjusted, which is not the case, controlling of power of an LED does not have much effect on the formed pattern, because the same area is illuminated by several LEDs.

Figure 2A:
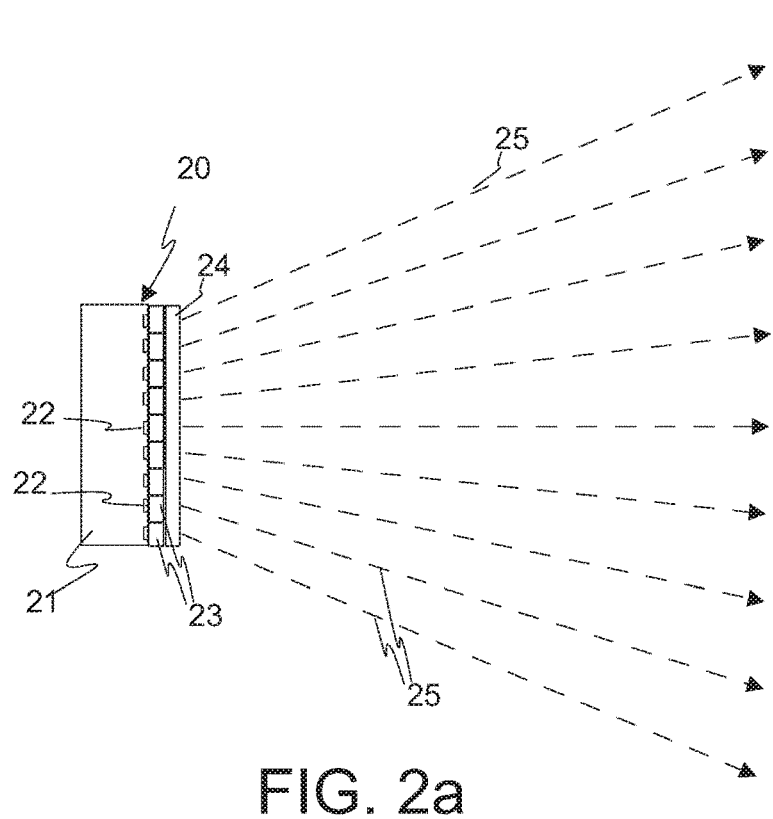
FIG. 2a, b show optical axes of LEDs of an LED matrix lighting device according to an example embodiment.
Figure 2B:
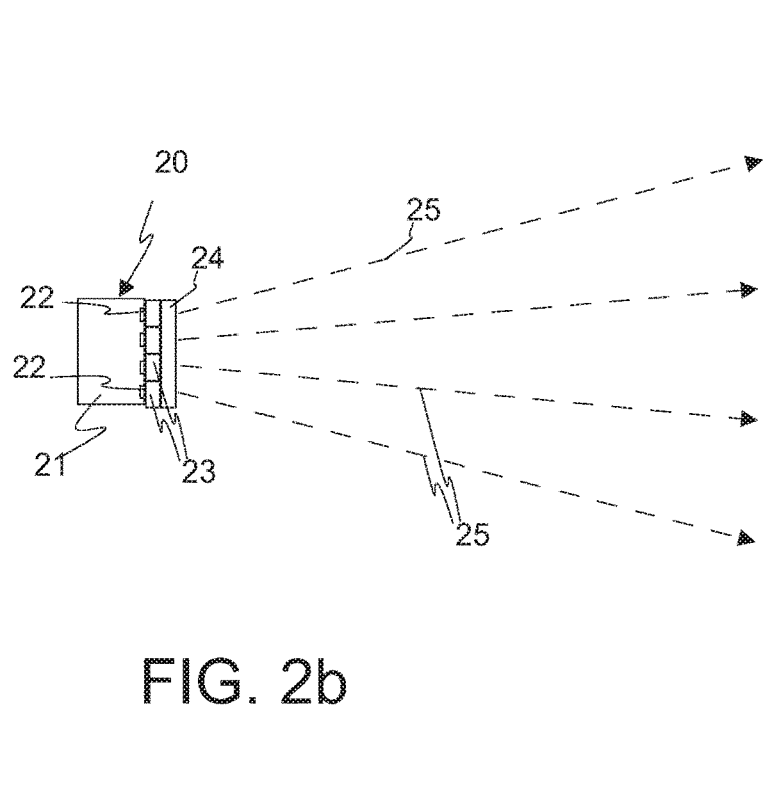
FIG. 2c, d show viewing angles of LEDs of the LED matrix lighting device of FIGS. 2a and 2b, correspondingly.

FIG. 2a shows, from above, the optical central axes 25 of light beams of LEDs 22 of an LED matrix lighting device 20 after light of LEDs 22 have passed through collimating lenses 23 and a light refracting element 24 according to an example embodiment of the present disclosure i.e. horizontal optical central axes 25 of the collimated and refracted LED light beams are shown. FIG. 2b shows those optical central axes 25 from a side i.e. vertical optical central axes 25 of the collimated and refracted LED light beams of the LEDs 22 are shown. The LED matrix lighting device 20 comprises a base 21, the LEDs 22, the collimating lenses 23, and the light refracting element 24. The size of the LED matrix is 9*4 (columns*lines) in this embodiment, but it may also be smaller or larger. In some embodiments, the number of columns may be, for example 1 to 25 and the number of lines may be, for example 1 to 25, or any other suitable number. In the smallest matrix, the number may be 2 i.e. the matrix is 2*1. The LEDs 22 may be attached, for example, onto a circuit board(s) or onto some other substrate (s) that is/are attached on the base 21.

There may be at least one powering circuit of LEDs 22 inside the base 21 and other possible electronic circuits, or the at least one powering circuit of LEDs 22 may be an external powering circuit of LEDs 22 that is electrically connected to LEDs 22. The at least one powering circuit is arranged to power the LEDs 22 so that each LED 22 illuminates at the required or desired intensity defined for it. The amount of current provided by at least one powering circuit may be controlled and/or determined by a data processing device integrated in the LED matrix lighting device 20 or by an external data processing device (not shown).

A collimating lens 23 is arranged in front of each LED 22 i.e. there is a matrix of collimating lenses 23, collimators, attached on the LED matrix to collimate output light of the LED. AN LED and a collimating lens together define the FWHM viewing angle of the LED i.e. a beam of light provided by each LED 22 and the viewing angle may be indicated by degrees, as explained above. It should be noted that the central axis of the collimated LED light beam corresponds to the central axis of the LED light that has not passed through the collimating lens.

The light refracting element 24 is arranged in front of each collimating lens 23 (and LEDs 22). In this embodiment the light refracting element 24 is a single refracting membrane attached in front of all LEDs 22 of the LED matrix and collimating lenses 23 of the matrix of collimating lenses 23. The light refracting element 24 may also be a matrix of refracting lenses/membranes attached on the matrix of collimating lenses 23. The light refracting element 24 is arranged to direct the central optical axes of collimated LED light beams incrementally outwards from the central axes of the collimated LED light (and the center of the LED matrix lighting device 20) so that a refraction angle is formed between the central optical axis of collimated LED light beam and the central axis 25 of the refracted LED light beam. The refraction angle is determined based on the place of an LED 22 in the LED matrix lighting device 20. For example, if an LED 22 is arranged to illuminate an area that is farther away, its refractive angle is greater than a refractive angle of an LED, which is arranged to illuminate an area that is closer, so that the area farther away can be illuminated. This refracting can be seen from FIGS. 2a and 2b, when comparing optical axes 25 of refracted LED light beams of LEDs 22 of FIGS. 2a and 2b to optical axes 14 of non-refracted LED light beams of LEDs 12 shown in FIGS. 1a and 1b. The light refracting element 24 is arranged to be easily changeable. This is because the size of the needed refraction angle caused by the light refracting element 24 depends on the distance of LED from the surface to be illuminated i.e. from the surface of the monitoring target and the distance may change if a position of the LED matrix lighting device is changed relative to a target surface 27. Different refraction angles can be achieved by different kind of light refracting elements. Refraction angles may be, for example, between 5 to 10°.

Figure 2C:
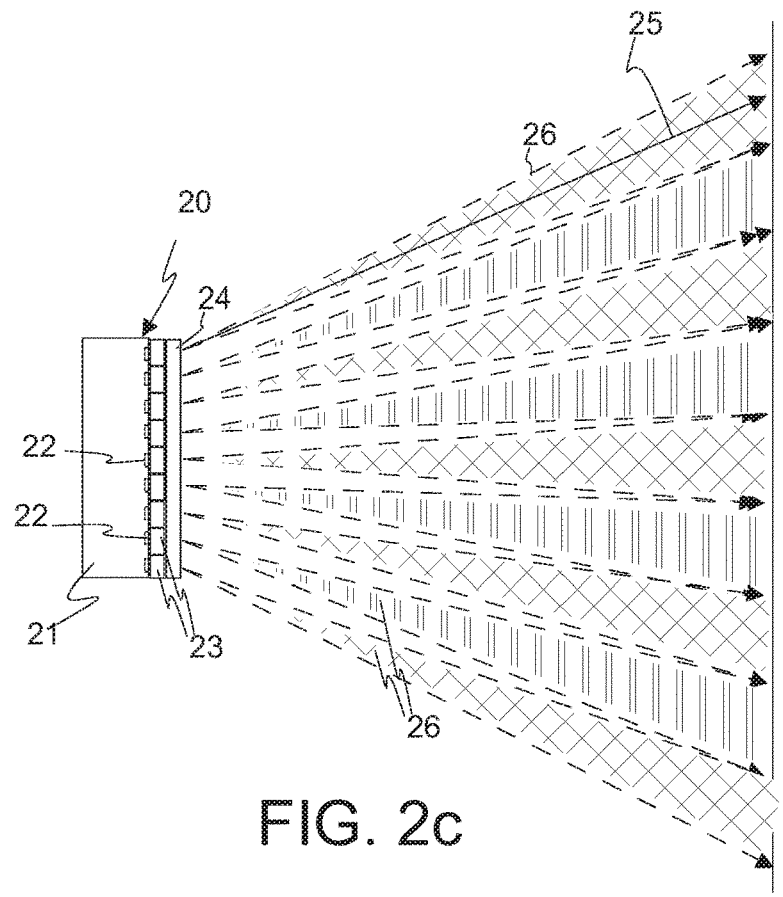
Figure 2D:
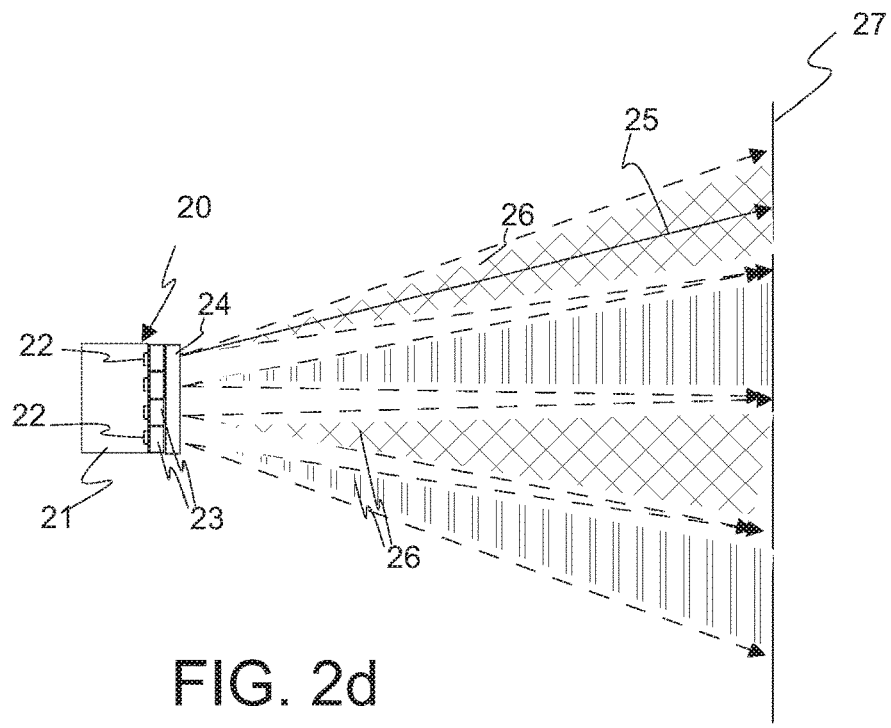

FIG. 2c shows viewing angles 26 of LEDs 22 of the LED matrix lighting device 20 of FIG. 2a and FIG. 2d shows viewing angles 26 of LEDs 22 of the LED matrix lighting device 20 of FIG. 2b. The viewing angles 26 of LEDs 22 have a conical shape; at first near the LED, it has a narrow shape and as the light extends away from the LED 22 it widens. One central axis 25 of the refracted LED light beam is shown in both FIGS. 2c and 2d.

The viewing angle 26 of every LED 22 in FIGS. 2c and 2d are indicated by a different check pattern. Because the central optical axes 25 of light beams of LEDs 22 are straight and refracted outwards by the light refracting element 24, the viewing angles 26 of LEDs 22 do not overlap when they achieve the target surface 27, and thus each part of the illumination pattern is illuminated only by one LED 22, and because each LED, column of LEDs or line of LEDs may be individually powered to provide desired intensity, the formed illumination pattern on the surface 27 may have an even luminous intensity. In addition, controlling of a power of an LED, a column of LEDS or a line of LEDs has a clear effect on intensity of the formed pattern on the target surface 27, because the viewing angles 26 of LEDs 22 do not overlap when they achieve the target surface 27 and thus each part of the illumination pattern is illuminated by one LED 22.

In this example embodiment, FWHM viewing angle of each LED 22 is 10 degrees, both in vertical and horizontal directions. In general, in LED matrix lighting devices according to embodiments of the present disclosure the FWHM viewing angle of light beams of LEDs are defined to be at least as large as the difference between the refraction angles of the optical axes of two adjacent LEDs. There is a difference between refraction angles of the optical axes of adjacent LEDs, because the light refracting element directs the central optical axes of collimated LED light beams to the side, for example, incrementally outwards from the optical central axis of the collimated LED light and the center of the lighting device differently depending on the place of the LED in the LED matrix and thus depending also on the distance from the monitoring target so that each LED illuminates a different part of the illumination pattern, i.e. viewing angles do not overlap. However, if the FWHM viewing angle of light beams of the LEDs are greater, for example, 20 degrees or more, the adjusting accuracy of the illumination pattern may reduce i.e. the intensity adjusting performed by power controlling of LEDs may not be so accurate.

Figure 3A:
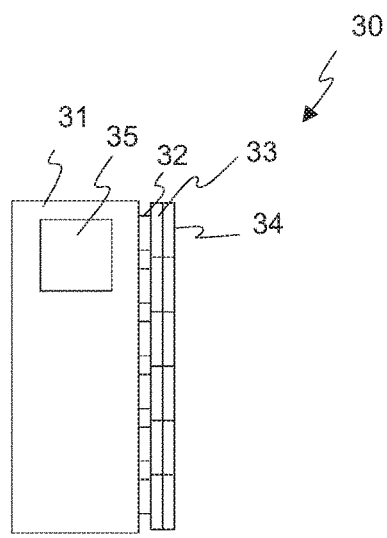
FIG. 3a shows an LED matrix lighting device according to an example embodiment.
Figure 3B:
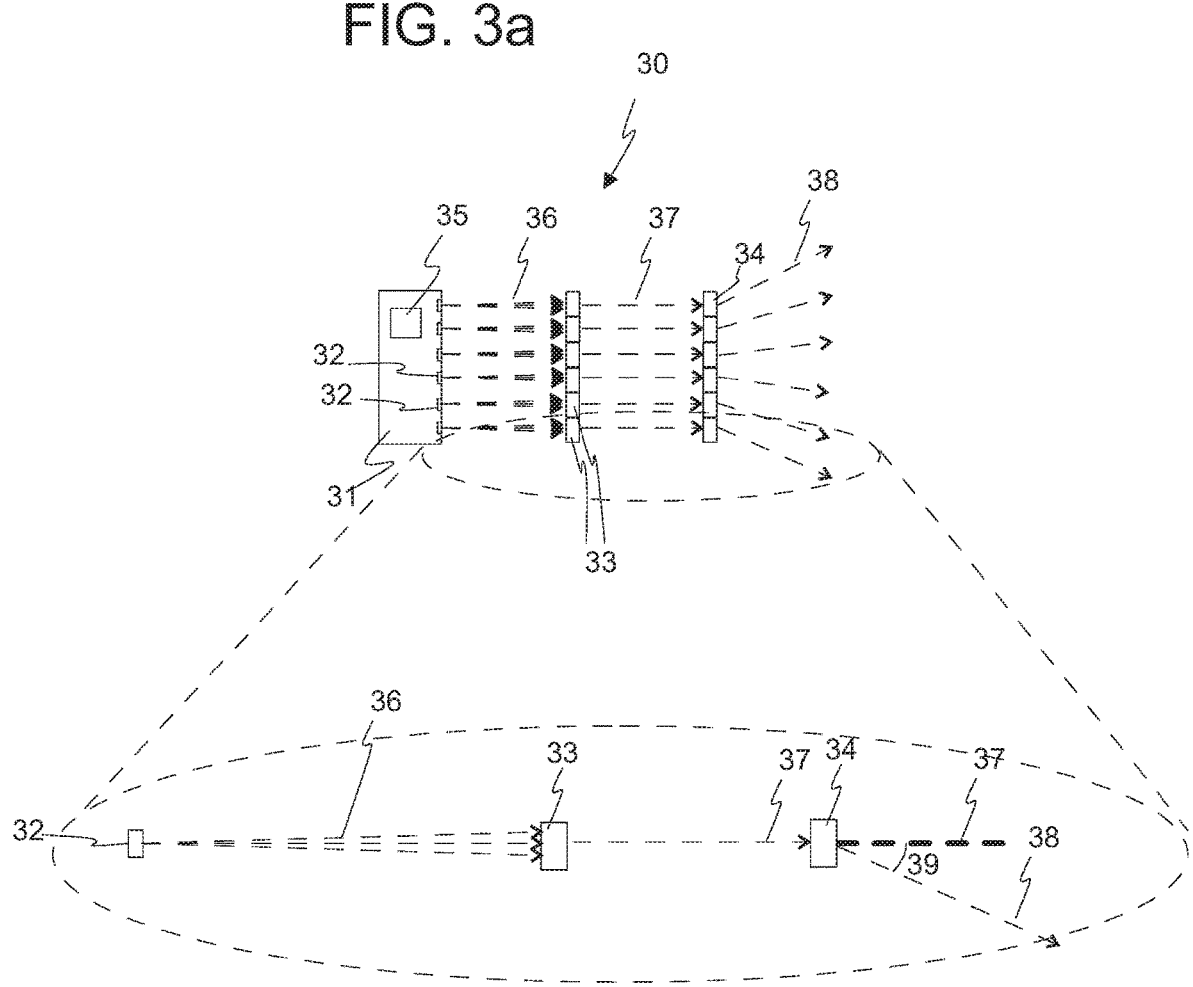

FIG. 3a shows an LED matrix lighting device 30 according to an example embodiment. The LED matrix lighting device 30 comprises a body 31, a matrix of LEDs 32, a matrix of collimating lenses 33, and a matrix of light refracting elements 34. LEDs 32 are arranged on the body 31, for example as such or by using a separate surface arranged to be attached on the body 31. The body 31 further comprises electronic circuits 35 arranged to power LED(s), but it may also comprise a data processing device that comprises at least one processor, at least one memory including computer program code for one or more program units, and means for receiving configuration information of how to power LEDs from a data processing device of a machine vision system or other external data processing device wirelessly or via wired connection from for example, a receiver or a transceiver. A collimating lens 33 of the collimating lens matrix is arranged in front of each LED 32 of the LED matrix. The light refracting element 34 of the light refracting element matrix is arranged in front of each collimating lens 33, on the other side of the collimating lens 33 than the LED 32, for refracting collimated light of the LED 32 in lateral direction from the optical central axis of collimated LED light 37 of the LED 32. The optical central axis of refracted light is indicated in FIG. 3b with reference number 38. The LED matrix lighting element 30 is connected to power supply. One or more light refracting elements 34 may have different refracting properties than other light refracting elements 34 i.e. one or more light refracting elements 34 may have different refracting properties compared to other light refracting elements, because the need to refract the optical central axis of collimated light 37 depends on a distance of an LED 32 (and light refracting element 34) from a target/area of the surface arranged to be illuminated. If there is only one light refracting element 34 instead of a matrix of light refracting elements 34, the refracting properties inside the element may vary.

Due to collimating lenses 33 and the refracting element 34, the LED matrix lighting device 30 illuminates an imaging target so that light illuminates the imaging target uniformly. However, for imaging, the intensity of illuminated pattern also has to be even, and therefore an amount of current provided for a first part of LEDs by the electronic circuits 35 is different than an amount of current provided for at least a second part of LEDs. Provided amount of current depends on, for example, the placement of an LED in the LED matrix of the lighting device and therefore also on an angle between the optical central axis of the LED (before refraction) and the optical central axis of refracted LED light beam, but also on the lighting angle i.e. how far from the imaging target the lighting device is positioned.

FIG. 3b shows an exploded view of the LED matrix lighting device 30 of FIG. 3a. In FIG. 3b are shown light rays 36 from the LEDs and optical axis of collimated LED light 37 and optical central axis of refracted LED light 38. Also a refraction angle 39 between the optical central axis of collimated LED light 37 and the optical central axis of refracted LED light 38 is shown.

Figure 4:
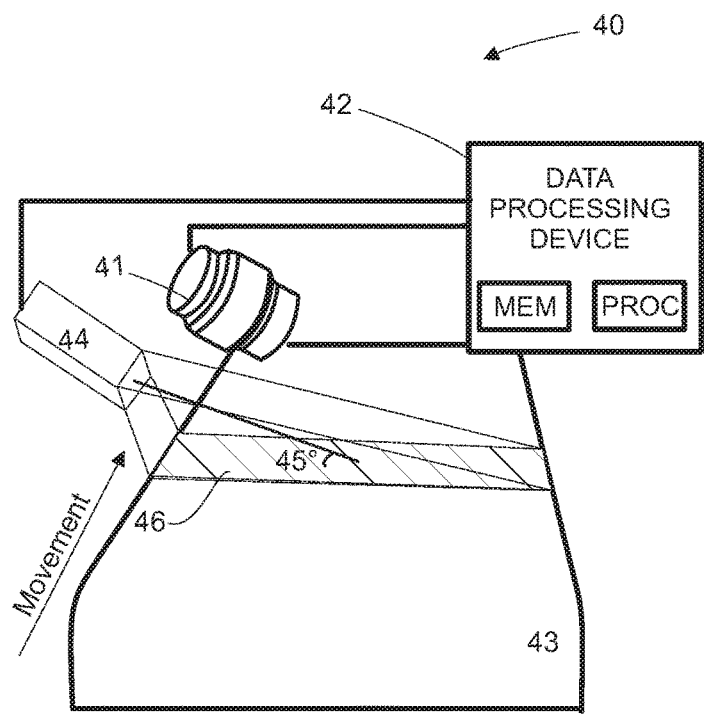
FIG. 4 shows a machine vision system comprising an LED matrix lighting device according to an example embodiment.

FIG. 4 shows a WMS or WIS machine vision system 40 disclosed in conjunction with a moving paper web 43 as a target object according to an embodiment. The moving direction of the web 43 is towards the image, away from the viewer of the image. The machine vision system 40 comprises a camera 41, an LED matrix lighting device 44 according to an embodiment of the present disclosure and a data processing device 42. The camera 41 is arranged to capture images from the illuminated paper web 43 and to transmit data of each image to the data processing device 42. The LED matrix lighting device 44 is a separate lighting device, but the lighting device 44 may also be an integrated part of the camera 41.

The data processing device 42 is configured to analyse the received image data captured and transmitted by the camera 41 in order to find deviations in the web 43. The data processing device 42 may further analyse the illumination pattern 46 in images. If a data processing device 42 detects from the image data that the pattern 46 does not have an even luminous intensity throughout the pattern, it may reconfigure electronic circuits of the LED matrix lighting devices 44 so that the amount of provided current to one or more LED changes and the intensity of the illumination pattern becomes constant throughout the pattern and deviations in the web 43 can be more accurately detected across the entire width of the web.

The data processing device 42 may control the power of LEDs, for example so that an amount of current provided for a first part of LEDs is different than an amount of current provided for at least a second part of LEDs. The provided amount of current may again depend on, for example, the placement of an LED in the LED matrix of the lighting device 44 i.e. on the refraction angle, and therefore also on the distance of an LED from the part of the paper web 43 it is configured to illuminate. Thus the LED matrix lighting device 44 according to an embodiment of the present disclosure and comprising LEDs, where a power supply is adjusted individually or as groups, is arranged to illuminate the paper web 43 (or other material web) for imaging by an illumination pattern 46 with uniform intensity, for example an illumination line with uniform intensity.

A lighting angle is the angle between the horizontal central axis of the LED matrix lighting devices 44 and the surface of the web 43. In this embodiment the angle is 45 degrees, 45°, but the angle may also be greater or smaller, and it may depend on the space arranged for the lighting device 44 or, for example, on the width of the illumination pattern arranged to be illuminated.

The data processing device 42 comprises at least one processor, at least one memory including computer program code for one or more program units, and means for receiving image data wirelessly or via wired connection from the camera 41, for example, a receiver or a transceiver, and means for transmitting trigger signals wirelessly or via wired connection, for example, a transmitter or a transceiver. There may be multiple processors e.g. a general purpose processor and a graphics processor and a DSP processor and/or multiple different memories e.g. volatile memory for storing data and programs at run-time and non-volatile memory such as a hard disk for permanently storing data and programs. The data processing device 42 is an external data processing device and it may be any computing device suitable for handling image data and possibly also determining or controlling current provided for LEDs, such as a computer. The data processing device 42 is in electronic communication with the camera 41 and the lighting device 44 via signal lines or wirelessly. The camera 41 may also include a video controller and an audio controller for generating signals that can be produced for the user with computer accessories. The camera 41 may produce output to the user through output means. The video controller may be connected to a display. The display may be e.g. a flat panel display or a projector for producing a larger image. The audio controller may be connected to a sound source, such as loudspeakers or earphones. The camera 44 may also include an acoustic sensor such as a microphone.

Figure 5:
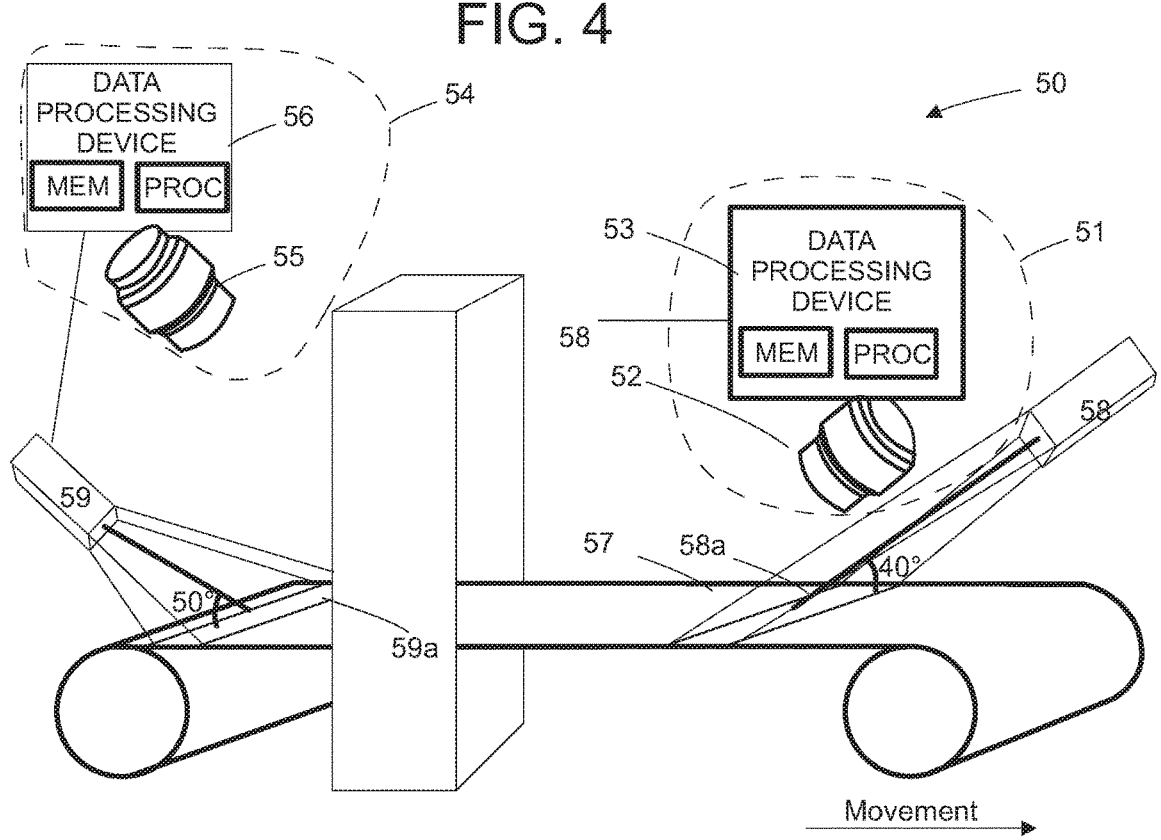
FIG. 5 shows a machine vision system comprising an LED matrix lighting device according to an example embodiment.

FIG. 5 shows an embodiment of the present disclosure, in which a WMS or WIS machine vision system 50 according to an embodiment is arranged to monitor a moving web 57. The machine vision system 50 comprises two LED matrix lighting devices 58, 59 according to an embodiment of the present disclosure and two smart cameras 51, 54 comprising an image sensor 52, 55 and a data processing device 53, 56. The LED matrix lighting devices 58, 59 may also be integrated parts of the smart cameras 51, 54. The LED matrix lighting device 58, 59 illuminates the moving web 57 in a lighting angle of 40 degrees and the LED matrix lighting device 59 illuminates the moving web 57 in a lighting angle of 50 degrees. The LED matrix lighting devices 58, 59 are located on the side even if not clearly seen from FIG. 5 i.e. they illuminate the pattern so that they are located away from the symmetry axis of the illuminated pattern. The image sensors 52, 55 are arranged to capture images from the moving web 57 and to transmit image data to the data processing device 53, 56 of the smart camera 51, 54.

The data processing devices 53, 56 may comprise similar structure and functionality as the data processing device 42.

The image sensors 52, 55 are arranged to capture images of the web 57 and the LED matrix lighting devices 58, 59 are illuminating the web 57 by the illumination patterns 58a, 59a on the surface of the web 57. The patterns 58a, 59a extend the whole width of the web 57. But it is also possible that the patterns are narrowed and extend the whole width of the web 57.

The various embodiments of the present disclosure can be implemented with the help of computer program code that resides in a memory and causes an apparatus to carry out the aspects of the disclosed embodiments. For example, the apparatus that is a computing device, for example, a data processing device may comprise circuitry and electronics for analysing, receiving and transmitting data, a computer program code in a memory, and a processor which, when running the computer program code, causes the apparatus to carry out the features of an embodiment.

Considerable advantages are achieved by the present disclosure when compared to methods and systems of existing LED matrix lighting devices or machine vision systems comprising at least LED matrix lighting devices. By means of the arrangement according to the aspects of the disclosed embodiments it is possible to place the LED matrix lighting device to the side of the web or other target to be illuminated, and still illuminate the whole pattern with uniform intensity, because the LED matrix lighting device has a light refracting element in front of collimating lenses (i.e. on the other side of the collimating lenses than LEDs) and LEDs that refracts optical central axes of LED light beams in a direction so that the areas illuminated by LEDs do not overlap or overlap only slightly, and because power of the LEDs can be controlled individually or as groups so that each LED illuminated the target with the same or essentially same intensity.

It is obvious that the present disclosure is not limited solely to the above-presented embodiments, but it can be modified within the scope of the appended claims.

The invention claimed is:

1. An LED matrix lighting device for illuminating a lighting pattern with even intensity, the LED matrix lighting device comprising a plurality of LEDs, a collimating lens in front of each LED for collimating light of the LED, and a light refracting element in front of collimating lenses arranged to refract light of at least a first part of the LEDs with a different refraction angle than at least a second part of the LEDs, and wherein current provided for at least one LED is adjustable based on detected intensity deviations in a captured image, and which a FWHM viewing angle of the collimated light of LEDs is substantially as large as the difference between the refraction angles.

2. The LED matrix lighting device according to claim 1, wherein the LED matrix lighting device further comprises at least one powering circuit of LEDs and an amount of current provided for the first part of LEDs is different than an amount of current provided for at least the second part of LEDs.

3. The LED matrix lighting device according to claim 1, wherein the first part of LEDs comprises one LED, one line of LEDs of the LED matrix or one column of LEDs of the LED matrix.

4. The LED matrix lighting device according to claim 1, wherein the refraction angle is determined based on the place of an LED in the LED matrix lighting device.

5. The LED matrix lighting device according to claim 1, wherein
a refraction angle is an angle between an optical central axis of collimated light of an LED and an optical central axis of the refracted light of the same LED.

6. The LED matrix lighting device according to claim 1, wherein current provided for at least one LED is adjustable.

7. A machine vision system for detecting deviations from a wood fibre web, wherein the machine vision system comprises:
an LED matrix lighting device for illuminating a lighting pattern with even intensity, the LED matrix lighting device comprises a plurality of LEDs, a collimating lens in front of each LED for collimating light of the LED, and a light refracting element in front of collimating lenses arranged to refract light of at least a first part of the LEDs with a different refraction angle than at least a second part of the LEDs, and wherein current provided for at least one LED is adjustable based on detected intensity deviations in a captured image, and which a FWHM viewing angle of the collimated light of LEDs is substantially as large as the difference between the refraction angles,
at least one imaging device for capturing images of the illuminated area, and
a data processing device.

8. The machine vision system according to claim 7, wherein the data processing device is arranged to analyse image data for detecting intensity deviations in the captured images.

9. A method comprising:
obtaining image data,
analyzing image data,
detecting intensity deviations in an illumination pattern provided by an LED matrix lighting device in the captured images, which LED matrix lighting device comprising a plurality of LEDs, a collimating lens in front of each LED for collimating light of the LED, and a light refracting element in front of collimating lenses arranged to refract light of at least a first part of the LEDs with a different refraction angle than at least a second part of the LEDs, and wherein current provided for at least one LED is adjustable based on detected intensity deviations in a captured image, and which a FWHM viewing angle of the collimated light of LEDs is substantially as large as the difference between the refraction angles, and
adjusting current provided for at least one LED of the LED matrix lighting device based on detected intensity deviations in a captured image.

10. A computer program product embodied on a non-transitory computer readable medium, comprising computer program code configured to, when executed on at least one processor, cause a system to perform the method comprising:
obtaining image data,
analyzing image data,
detecting intensity deviations in an illumination pattern provided by an LED matrix lighting device in the captured images, which LED matrix lighting device comprises a plurality of LEDs, a collimating lens in front of each LED for collimating light of the LED, and a light refracting element in front of collimating lenses arranged to refract light of at least a first part of the LEDs with a different refraction angle than at least a second part of the LEDs, and wherein current provided for at least one LED is adjustable based on detected intensity deviations in a captured image, and which a FWHM viewing angle of the collimated light of LEDs is substantially as large as the difference between the refraction angles, and adjusting current provided for at least one LED of the LED matrix lighting device based on detected intensity deviations in a captured image.

\* \* \* \* \*